US008308783B2

(12) United States Patent
Morris et al.

(10) Patent No.: US 8,308,783 B2
(45) Date of Patent: Nov. 13, 2012

(54) COLLAPSIBLE BONE SCREW APPARATUS

(75) Inventors: Stephen Morris, Chico, CA (US); Tom Weisel, Ventura, CA (US); Roger Pisarnwongs, Valencia, CA (US)

(73) Assignee: Arch Day Design, LLC, Ventura, CA (US)

( * ) Notice: Subject to any disclaimer, the term of this patent is extended or adjusted under 35 U.S.C. 154(b) by 362 days.

(21) Appl. No.: 12/538,629

(22) Filed: Aug. 10, 2009

(65) Prior Publication Data

US 2010/0036440 A1    Feb. 11, 2010

Related U.S. Application Data

(60) Provisional application No. 61/188,724, filed on Aug. 11, 2008, provisional application No. 61/189,074, filed on Aug. 15, 2008.

(51) Int. Cl.
*A61B 17/04* (2006.01)
*A61B 17/84* (2006.01)
*A61F 2/08* (2006.01)

(52) U.S. Cl. .................. 606/328; 606/304; 606/105

(58) Field of Classification Search ................ 606/320, 606/63, 65, 66, 310, 315, 316, 322, 324
See application file for complete search history.

(56) References Cited

U.S. PATENT DOCUMENTS

| 2,397,545 A | 4/1946 | Hardinge |
| 2,511,051 A | 6/1950 | Dzus |
| 2,834,342 A | 5/1958 | Yost |
| 3,051,169 A | 8/1962 | Grath |
| 3,530,854 A | 9/1970 | Kearney |
| 4,175,555 A | 11/1979 | Herbert |
| 4,456,005 A | 6/1984 | Lichty |
| 4,463,753 A | 8/1984 | Gustilo |
| 4,530,355 A | 7/1985 | Griggs |
| 4,628,923 A | 12/1986 | Medoff |
| 4,640,271 A | 2/1987 | Lower |
| 4,790,304 A | 12/1988 | Rosenberg |
| 4,940,467 A | 7/1990 | Tronzo |
| RE33,348 E | 9/1990 | Lower |

(Continued)

OTHER PUBLICATIONS

Notification of Transmittal of the International Search Report and the Written Opinion of the International Searching Authority, International Search Report (date mailed Sep. 28, 2009) and Written Opinion of the International Searching Authority for PCT/US09/53300, filed on Aug. 10, 2009.

(Continued)

*Primary Examiner* — Andrew Yang
*Assistant Examiner* — Olivia C Chang
(74) *Attorney, Agent, or Firm* — Vic Y. Lin; Innovation Capital Law Group, LLP

(57) ABSTRACT

A collapsible bone screw for healing bone fragments across a bone fracture includes an externally threaded inner screw member and an externally threaded outer screw member. The inner screw member is initially screwed into an inner bone portion. An unthreaded portion of the outer screw member is movably joined to the inner screw member. The outer screw member is screwed until it gains purchase in an outer bone portion. As impaction occurs over time, the collapsible bone screw apparatus may shorten in length as the two screw members slide, telescope or otherwise axially move toward each other to shorten the overall length, thereby preventing any portion of the screw apparatus from protruding out of the bone. A bone screw kit of multiple inner and outer screw members are provided as well as a method of surgically fastening bone fragments.

33 Claims, 8 Drawing Sheets

U.S. PATENT DOCUMENTS

| | | |
|---|---|---|
| 5,007,910 A | 4/1991 | Anapliotis et al. |
| 5,032,125 A | 7/1991 | Durham et al. |
| 5,122,141 A | 6/1992 | Simpson et al. |
| 5,167,664 A | 12/1992 | Hodorek |
| 5,263,955 A | 11/1993 | Baumgart et al. |
| 5,425,732 A | 6/1995 | Ulrich |
| 5,498,265 A | 3/1996 | Asnis et al. |
| 5,531,748 A | 7/1996 | de la Caffiniere |
| 5,540,687 A | 7/1996 | Fairley et al. |
| 5,626,580 A | 5/1997 | Brosnahan |
| 5,743,912 A | 4/1998 | Lahille et al. |
| 5,827,285 A | 10/1998 | Bramlet |
| 5,935,129 A | 8/1999 | McDevitt et al. |
| 5,961,553 A | 10/1999 | Coty et al. |
| 6,183,476 B1 | 2/2001 | Gerhardt et al. |
| 6,224,606 B1 | 5/2001 | Horiuchi |
| 6,319,254 B1 | 11/2001 | Giet et al. |
| 6,524,313 B1 | 2/2003 | Fassier et al. |
| 6,887,243 B2 | 5/2005 | Culbert |
| 7,318,825 B2 | 1/2008 | Butler et al. |
| 7,575,572 B2 | 8/2009 | Sweeney |
| 2005/0010224 A1* | 1/2005 | Watkins et al. .................. 606/65 |
| 2005/0143735 A1 | 6/2005 | Kyle |
| 2005/0277940 A1* | 12/2005 | Neff .............................. 606/73 |
| 2007/0239161 A1 | 10/2007 | Giger et al. |
| 2008/0039846 A1 | 2/2008 | Lee et al. |
| 2008/0119855 A1 | 5/2008 | Hoegerle et al. |
| 2008/0177333 A1 | 7/2008 | Ferguson |

OTHER PUBLICATIONS

DePuy Orthopaedics, Inc., "DePuy launches the only technology to treat intertrochanteric hip fractures using traditional or minimally invasive procedures"; Press Release of DePuy Orthopaedics, Inc, Jul. 20, 2007.

* cited by examiner

COLLAPSIBLE BONE SCREW APPARATUS

RELATED APPLICATIONS

This application relates to, claims priority from, and incorporates herein by reference, as if fully set forth, the following:
1) U.S. Provisional Patent Application Ser. No. 61/188,724 filed on Aug. 11, 2008 and entitled "COLLAPSING BONE SCREW"; and
2) U.S. Provisional Patent Application Ser. No. 61/189,074 filed on Aug. 15, 2008 and entitled "COLLAPSING BONE SCREW".

BACKGROUND OF THE INVENTION

1. Field of the Invention

The invention relates generally to surgical devices and methods, and more particularly to bone screws for surgically fastening bone fractures.

2. Description of Prior Art and Related Information

Conventionally, a bone screw used to surgically fasten together fractured bone fragments consists of a one-piece device having two ends. The screw has a set of threads at its proximal end—i.e., the end that will be nearest the center of the body when the screw is in place.

In use, a guide pin is inserted across the fracture and into the bone or bone fragment that will receive the proximal end of the screw. The self-tapping bone screw is then inserted over the guide pin and rotated such that the proximal threads gain purchase. The distal end of the screw is designed and the screw's length is selected such that the bone screw allows compression of the bone fragments together. When insertion is complete, the screw is completely embedded within the compressed fragments.

However, over time, impaction can take place near the fractured bone surfaces, which may cause the distal end of the screw to protrude from the bone in which it was initially embedded. When this occurs, the protruding portion can cause pain to the patient, interfere with ambulation, and may require a second surgery for removal of the screw.

SUMMARY OF THE INVENTION

In accordance with the present invention, structures and associated methods are disclosed which address these needs and overcome the deficiencies of the prior art.

In one aspect, a collapsible bone screw apparatus is provided. The apparatus comprises an inner screw member and an outer screw member axially movable with respect to the inner screw member in order to provide an adjustable total length of the apparatus. The inner screw member has an externally threaded portion adjacent to a medial end, a non-threaded portion adjacent to a lateral end, and an inner screw opening configured to enable the inner screw member to be screwed. The outer screw member has an outer screw threaded portion and a lateral outer screw opening configured to enable the outer screw member to be screwed. The apparatus further comprises a stop to provide a minimum for the total length.

The inner screw member opening and the outer screw opening may be configured to mate with a first fastener and second fastener, respectively. Alternatively, the inner screw member and the outer screw member may be configured to mate with the same fastener. The inner screw member and outer screw member are substantially hollow. The inner screw opening may comprise a first polygonal shaped opening. The outer screw opening may comprise a second polygonal shaped opening.

In one embodiment, the outer screw member is configured to slide within the inner screw member. In another embodiment, the inner screw member is configured to slide within the outer screw member.

The inner screw member comprises a hollow chamber having a lateral end and a medial end. In one embodiment, the inner screw opening is located adjacent to the medial end of the hollow chamber. In this embodiment, the inner screw opening has a cross-dimension, or width, less than an inner diameter of the hollow chamber.

In a further embodiment, the inner screw opening is located adjacent to the lateral end of the hollow chamber, in which case the inner screw opening has a cross-dimension, or width, greater than an inner diameter of the hollow chamber.

In a further aspect, a collapsible bone screw kit is provided comprising a variety of inner screw members and outer screw members. The kit comprises a first inner screw member having a first length and a first external portion configured to secure the first inner screw member to a first bone portion. The kit also includes a second inner screw member having a second length longer than the first length, and a second external portion configured to secure the second inner screw member to the first bone portion. The kit comprises an outer screw member having an externally threaded portion configured to secure the outer screw member to a second bone portion. The outer screw is configured to be movably joined to one of the first inner screw member and the second inner screw member.

The first inner screw member comprises a first inner screw opening configured to mate with a fastener. The second inner screw member comprises a second inner screw opening configured to mate with the fastener. The outer screw member comprises an outer screw opening configured to mate with the fastener. The first inner screw member and the outer screw member form a first maximum length when joined. The second inner screw member and the outer screw member form a second maximum length greater than the first maximum length when coupled.

The kit further comprises a stop to limit overlap between the outer screw member and one of the first and second inner screw members. The stop may comprise a first internal shoulder formed in the first inner screw member, and a second internal shoulder formed in the second inner screw member. The stop may also comprise an external shoulder formed in the outer screw member. The stop may also comprise a first external shoulder formed in the first inner screw member, and a second external shoulder formed in the second inner screw member.

The kit may further comprises a second outer screw member with a second outer screw length greater than the outer screw length of the first outer screw member.

The first external portion of the first inner screw member may comprise a first externally threaded portion. The second external portion of the second inner screw member may comprise a second externally threaded portion.

In a further aspect, a method is provided for surgically fastening bone fragments. The method comprises screwing a threaded inner screw member into a first bone portion, movably joining a threaded outer screw to the inner screw member, screwing the outer screw member into a second bone portion after screwing the threaded inner screw member, and preventing the outer screw member from protruding out of the second bone portion over time by decreasing a total length between the inner screw member and the outer screw member.

The step of screwing the threaded inner screw member into the first bone portion comprises screwing a medial opening of the inner screw member with a fastener. The step screwing the threaded outer screw member into the second bone portion comprises screwing a lateral opening of the outer screw member with a fastener.

The method further comprises selecting the inner screw member from a plurality of inner screw members having different lengths, and selecting the outer screw member from a plurality of outer screw members having different lengths.

The step of preventing the outer screw member from protruding out of the second bone portion over time comprises sliding the outer screw member into the inner screw member, or sliding the outer screw member over the inner screw member.

The further comprises limiting movement of the outer screw member and inner screw member toward each other at a predetermined position.

A collapsible bone screw for healing bone fragments across a bone fracture includes an externally threaded inner screw member and an externally threaded outer screw member. The inner screw member is initially screwed into an inner bone portion. An unthreaded portion of the outer screw member is movably joined to the inner screw member. The outer screw member is screwed until it gains purchase in an outer bone portion. As impaction occurs over time, the collapsible bone screw apparatus may shorten in length as the two screw members slide, telescope or otherwise axially move toward each other to shorten the overall length, thereby preventing any portion of the screw apparatus from protruding out of the bone. A bone screw kit of multiple inner and outer screw members are provided as well as a method of surgically fastening bone fragments.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

Figure 1:
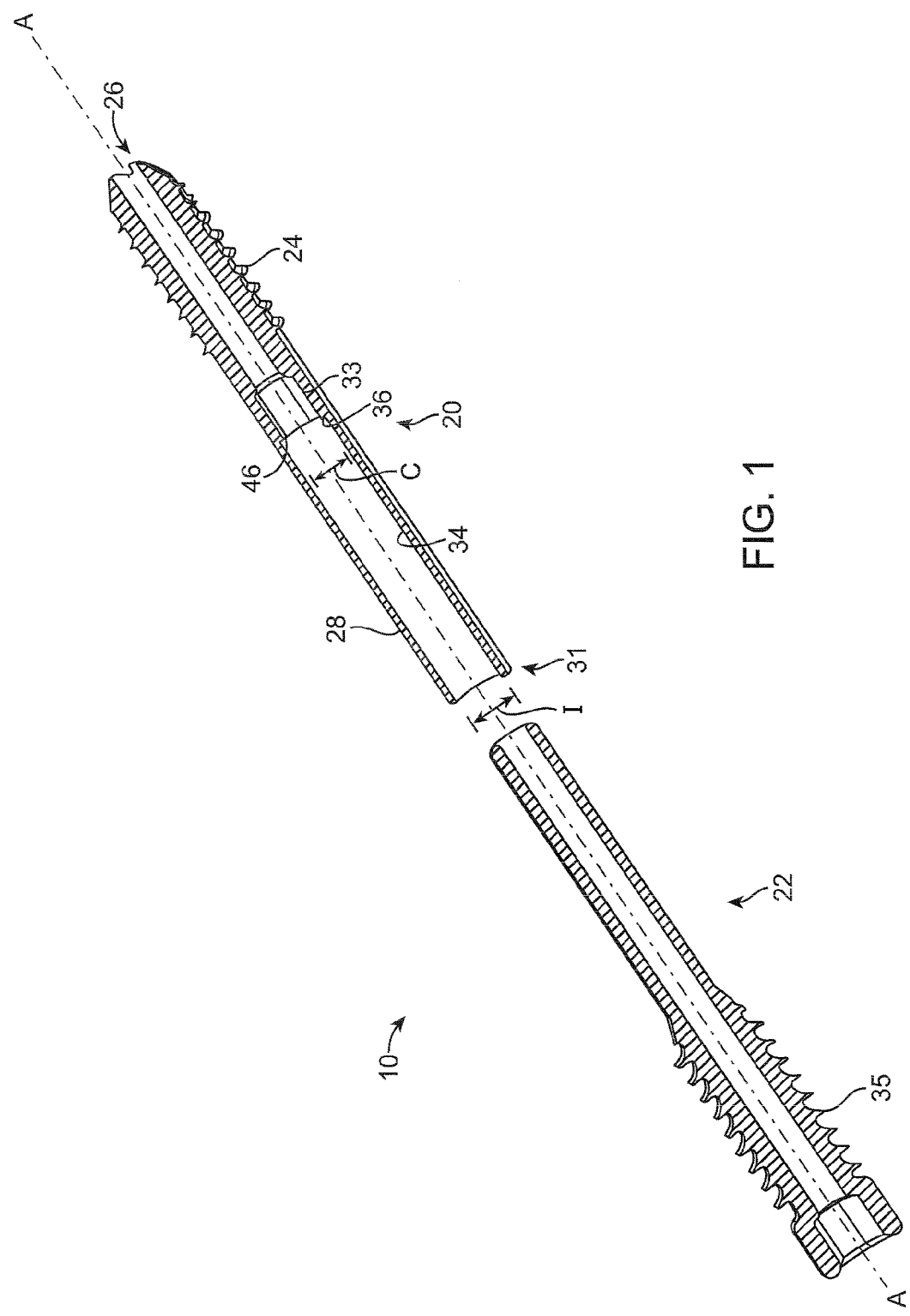
FIG. 1 is a cutaway exploded view of a first preferred embodiment of a collapsible bone screw apparatus.

A first preferred embodiment of a collapsible bone screw apparatus is illustrated in FIG. 1 and designated generally by the reference numeral 10. The multi-piece screw apparatus 10 is configured for fastening together bone fragments, particularly where impaction occurs to effect healing, such as in the femoral neck. As used throughout the specification, the terms "inner," "inward" and "medial" refer to the center of the patient for which the apparatus is used, whereas "outer," "outward" or "lateral" refer to a location and direction away from the center of the patient.

In FIG. 1, the bone screw apparatus 10 comprises an inner, or medial, screw member 20 and an outer, or lateral, screw member 22, which are configured to be joined to each other and movably adjustable along an axis "A." The inner screw member 20 preferably comprises a shaft including an externally threaded portion 24 having a first plurality of external threads adjacent to a far end 26. The external portion 24 may also comprise other means for attaching to bone, such as a barb or tack. An unthreaded external portion 28 extends from a lateral end 31 to the threaded portion 24. In the preferred embodiment, the inner screw member 20 is configured to receive a fastener, or driving tool, such as a hex key, so that the inner screw member 20 may be deployed initially and independently from the outer screw member 22. Accordingly, an inner screw opening, or socket, 33 is configured to mate with a driving tool. In the preferred embodiment, the socket 33 is defined deep within the inner screw member 20 and may be hex shaped, for example, to mate with a hex key.

In the first preferred embodiment shown in FIG. 1, the inner screw member 20 is configured to slidably receive the outer screw member 22. Accordingly, the inner screw 20 comprises a cylindrically shaped hollow chamber 34 starting from the lateral end 31 to a medial end 36 of the chamber 34. The hollow chamber 34 can comprise any other shape. The socket 33, which preferably has a polygonal shape and a cross-dimension different from that of the chamber 34, is preferably located adjacent to the medial end 36 of the chamber 34 so as not to interfere with the chamber 34 receiving the outer screw member 22. The exterior of the inner screw member 20 is preferably circular in profile, although it may take on any particular shape. In the first preferred embodiment, the socket 33 has a cross-dimension, or width, "C" that is less than an inner diameter "I" of the chamber 34.

Figure 3:
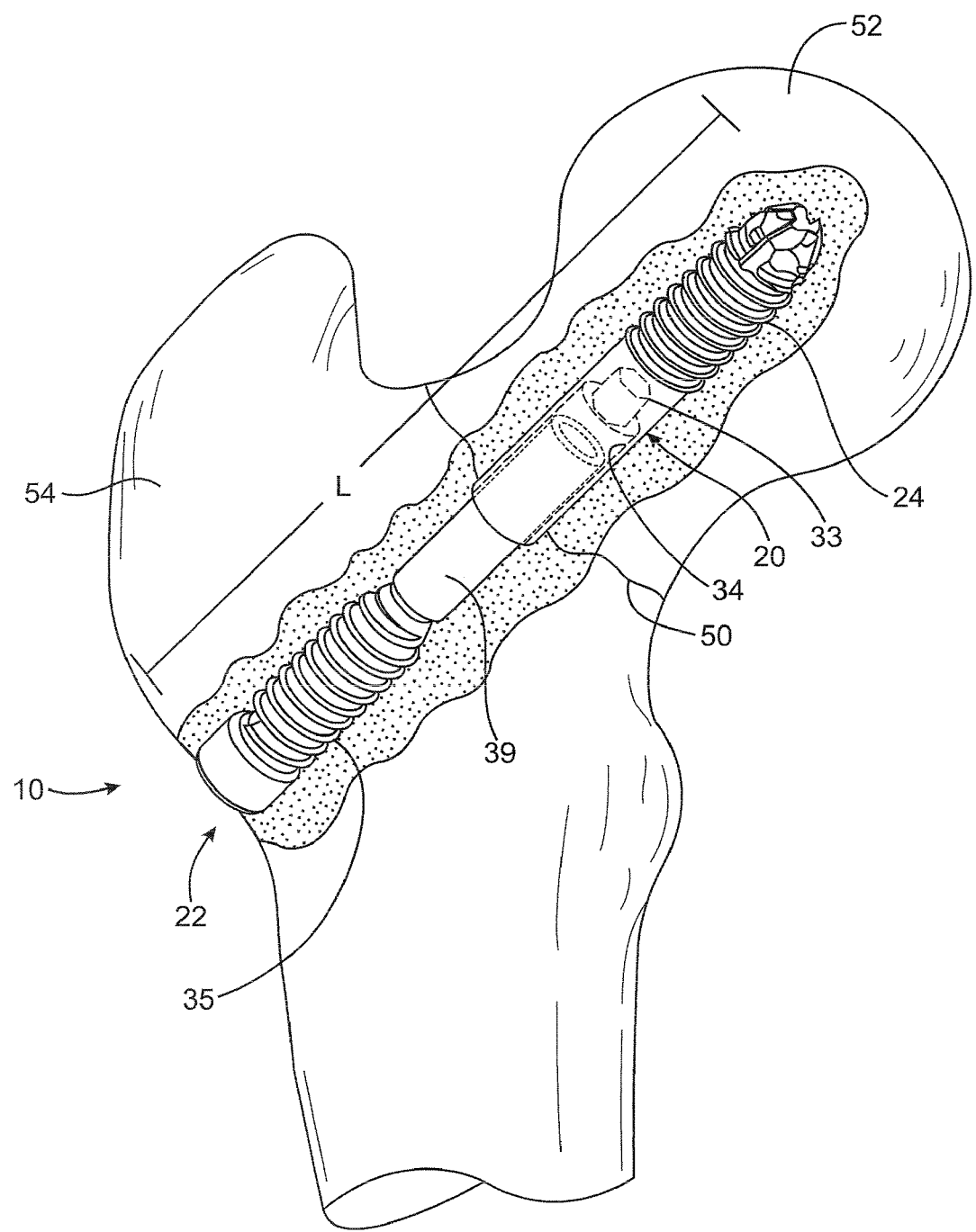
FIG. 3 is an operative view of the first preferred embodiment of the collapsible bone screw apparatus.

The outer screw member 22 is configured to be joined and axially movably with respect to the inner screw member 20. In particular, the outer screw member 22 is preferably slidable with respect to the inner screw along the axis "A" defined by the apparatus 10, so as to provide a variable length "L" of the entire apparatus 10 when deployed, as shown in FIG. 3.

Figure 2:
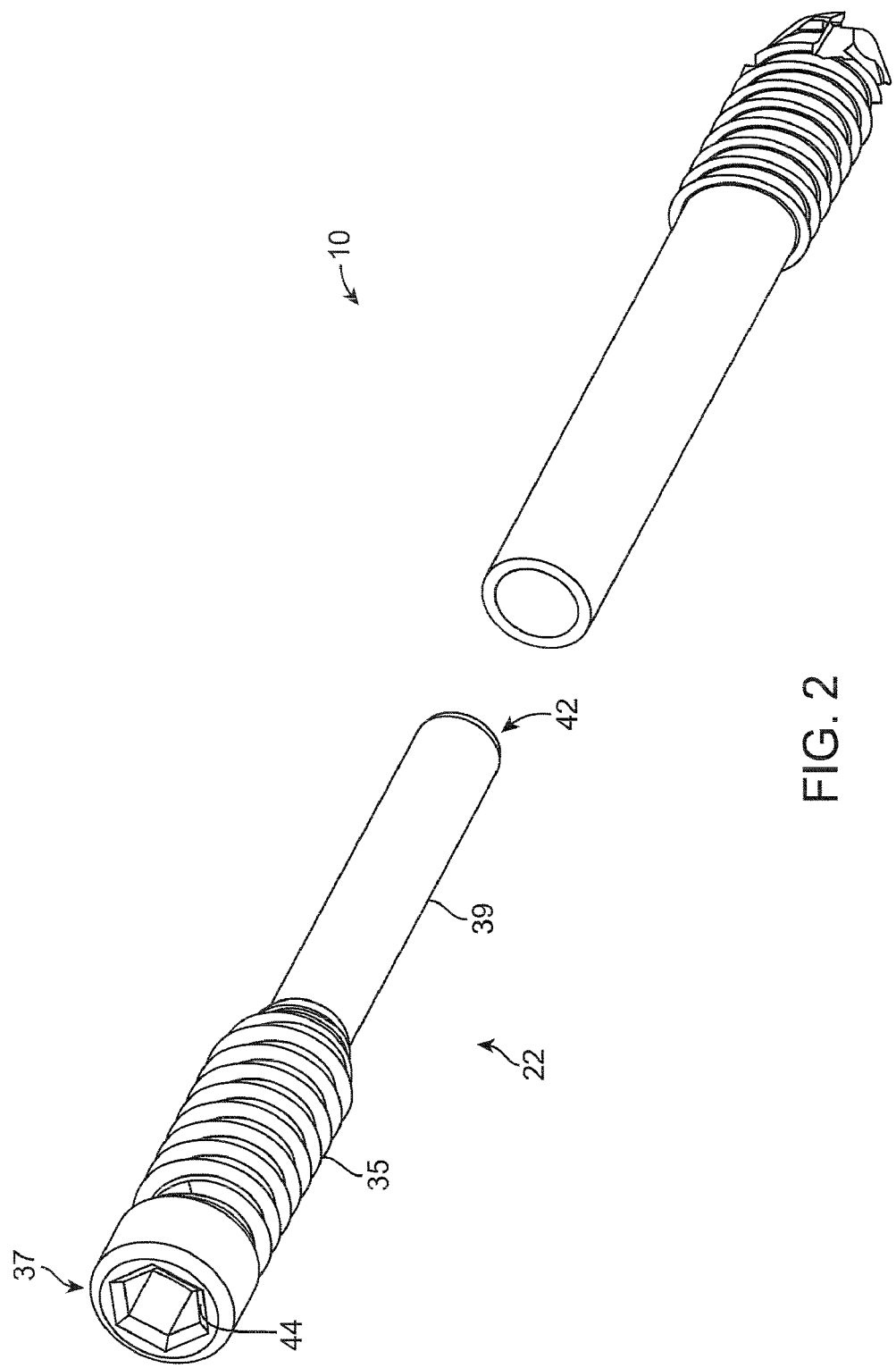
FIG. 2 is an exploded perspective view of the first preferred collapsible bone screw apparatus, showing the inner screw member and the outer screw member.

In FIG. 2, the outer screw member 22 preferably comprises a shaft including an externally threaded portion 35 having a second plurality of threads preferably adjacent to a lateral end, or outer screw opening, 37. An unthreaded external portion 39 extends from a medial end 42 to the threaded portion 35. In the preferred embodiment, the lateral end 37 is configured to receive a fastener, or driving tool, such as a hex key. Accordingly, the lateral end 37 may comprise a hex shaped lateral opening 44 to mate with a hex key. For convenience, the lateral outer screw opening 44 may be configured to receive the same drive tool as the medial opening 33 of the inner screw member 20, shown in FIG. 1, although the two openings 44, 33 may have completely different shapes and sizes to receive different drive tools.

In the preferred embodiment, the outer screw member 22 is at least hollow starting from the lateral end 37 and preferably through to the medial end 42. The exterior of the outer screw member 22 is preferably circular in profile, although it may take on any particular shape.

The preferred bone screw apparatus 10 is axially collapsible so as to provide a variable total length when assembled and deployed. As an example and not by way of limitation, the apparatus 10 is made collapsible by virtue of the inner screw member 20 and the outer screw member 22 being slidable with respect to each other. In the first preferred embodiment as shown in FIG. 1, the outer screw member 22 is configured to slide, or telescope, within the hollow chamber of the inner screw member 20. Accordingly, the inner diameter of the inner screw member 20 is larger than the outer diameter of the outer screw member 22 so as to allow the outer screw member 22 to slide freely within, but preferably not so large as to allow excessive side-to-side play between the two screw members 20, 22.

Alternatively, it is to be expressly understood that the outer screw member 22 may be configured to slide over the inner screw member 20, in which case the inner diameter of the outer screw member 22 would be larger than the outer diameter of the inner screw member 20.

In either case, the pair of screw members 20, 22 are movably joined to each other in the preferred embodiments so as to enable the overall length of the bone screw apparatus 10 to self-adjust, particularly shorten, as a result of bone impaction.

In the first preferred embodiment in FIG. 1 where the outer screw member 22 is configured to slide within the inner screw member 20, a stop 46 may be provided to limit the extent of overlap between the inner screw member 20 and the outer screw member 22. The stop 46 may comprise an inner ledge formed in the inner surface of the inner screw member 20 at the medial end 36 of the hollow chamber 34. The inner ledge 46 is preferably annular and may be located at a predetermined position so as to provide a minimum total length of the apparatus 10, or a minimum distance between the two threaded portions 24, 35. A similar inner ledge can be placed inside the outer screw member 22 (not shown) for the situation where the inner diameter of the outer screw member 22 is larger than the outer diameter of the inner screw member 20.

A preferred method of surgically fastening bone fragments is illustrated in FIG. 3 which depicts the first preferred embodiment of the apparatus 10 in operation. FIG. 3 illustrates an exemplary bone fracture 50 for which the bone screw apparatus 10 may be used. The fracture 50 is shown as dividing a bone into a first, or medial, bone portion 52 and second, or lateral, bone portion 54. A guide pin may be initially inserted across the fracture 50.

Preferably hollow throughout, the inner screw member 20 is screwed along a guide pin into the medial bone portion 52, e.g., the femoral head of a hip bone. The inner screw member 20 is rotated until its externally threaded portion 24 sufficiently gains purchase near the desired location just short of the cortical wall. For example, a driving tool such as a hex key is engaged with the medial socket 33 and rotated, thereby rotating the inner screw member. The driving tool is then removed. As shown in FIG. 3, the external threads 24 on the inner screw member 20 are directly attached to the medial bone portion 52.

The outer screw member 22, also preferably hollow throughout, is then slid over the guide pin, with the smooth unthreaded portion 39 sliding into to the inner screw member 20, e.g., via sliding into the chamber 34 of the inner screw member 20. By locating the socket 33 at a medial end of the chamber 34, the socket 33 does not get in the way of the inner screw member 20 receiving the outer screw member 22, particularly since the socket 33 preferably has a different cross-dimension and shape than those of the chamber 34. The outer screw member 22 is rotated until its externally threaded portion 35 sufficiently gains purchase in the outer bone portion 54 near the desired location, e.g., lateral cortex of hip bone, and is seated properly. As shown in FIG. 3, the external threads 35 on the outer screw member 22 are directly attached to the outer bone portion 54.

When insertion is complete, the collapsible apparatus 10 provides a variable total length as the two screw members 20, 22 are axially movable with respect to each other. This prevents any one the screw members 20, 22, particularly the outer screw member 22, from protruding out of the bone due to impaction of the bone over time. It will be appreciated that the apparatus 10 controls impaction of the bone fragments together across the fracture to facilitate healing. As impaction occurs near the surfaces of the fractured bone, the screw members 20, 22 collapse, or telescope within one another, to reduce the overall length of the apparatus 10 and to prevent any particular screw member 20, 22 from protruding out of the bone surface.

Figure 4:
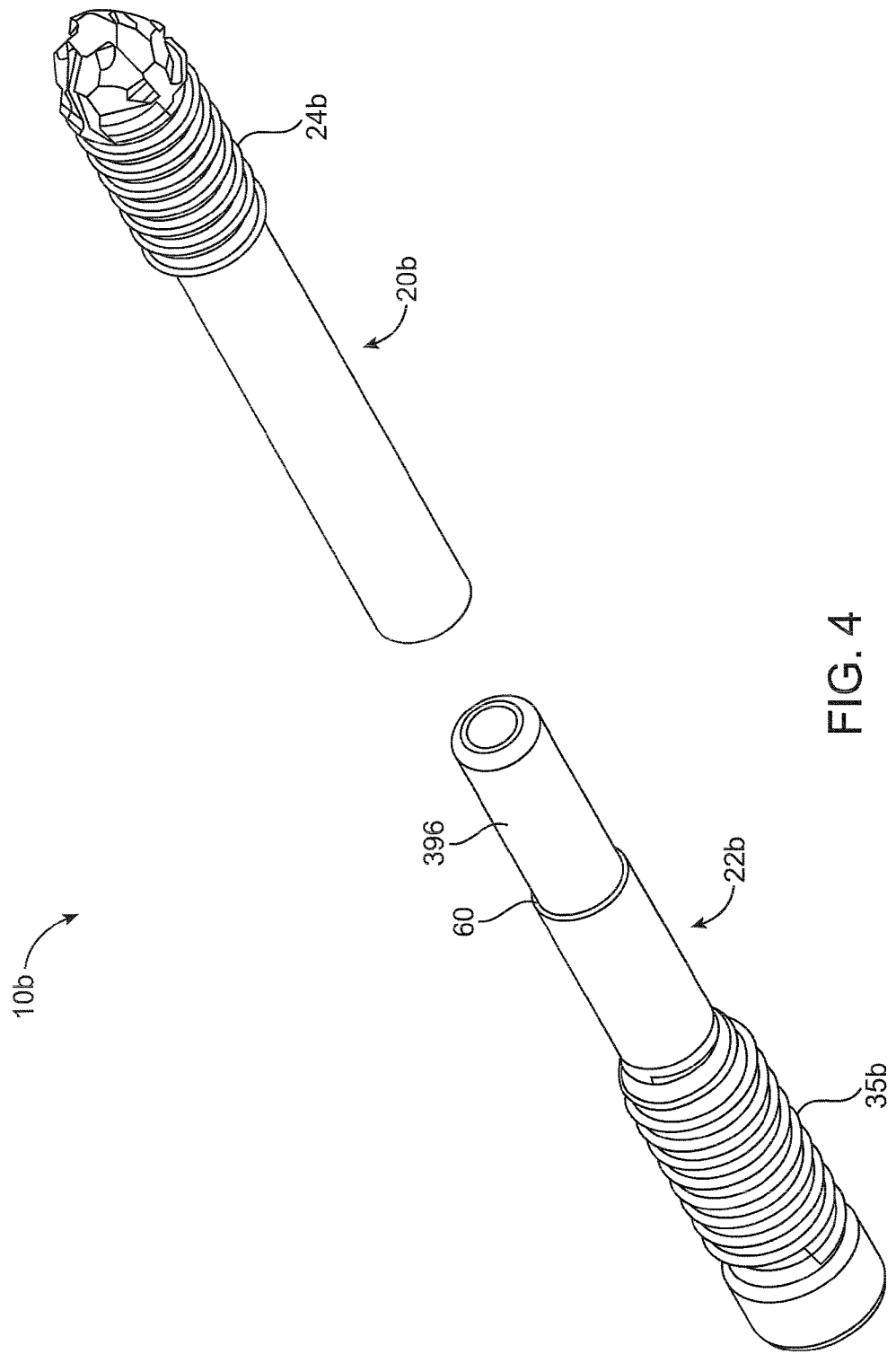
FIG. 4 is an exploded perspective view of a second preferred embodiment of a collapsible bone screw apparatus showing an external stop on an outer screw member.

In a second preferred embodiment of the bone screw apparatus illustrated in FIG. 4, elements of similar structure as the first embodiment are designated by the same reference numerals followed by the lower case "b". In FIG. 4, a bone screw apparatus 10b comprises a stop 60 to limit the extent of overlap between the inner screw member 20b and the outer screw member 22b. In the second preferred embodiment 10b where the outer screw member 22b is configured to slide within the inner screw member 20b, the stop 60 comprises an annular shoulder formed on external unthreaded portion 39b of the outer screw member 22b. The shoulder 60 may be located at a predetermined position so as to provide a minimum total length of the apparatus 10b, or a minimum distance between the two threaded portions 24b, 35b.

Figure 5:
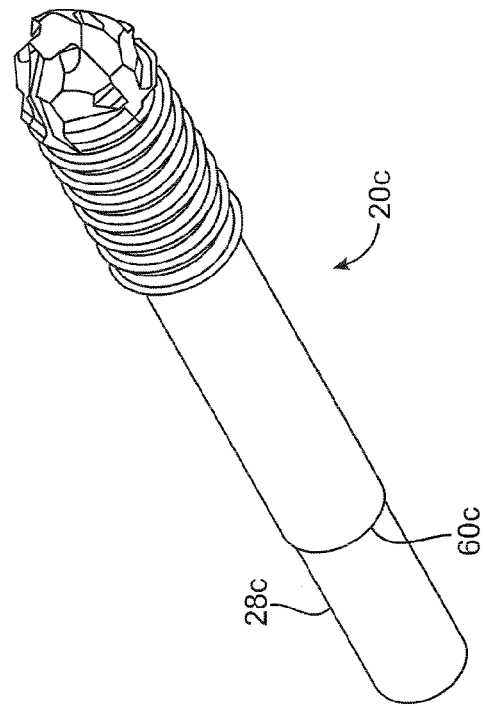
FIG. 5 is an exploded perspective view of a third preferred embodiment of a collapsible bone screw apparatus showing an external stop on an inner screw member.
Figure 5:
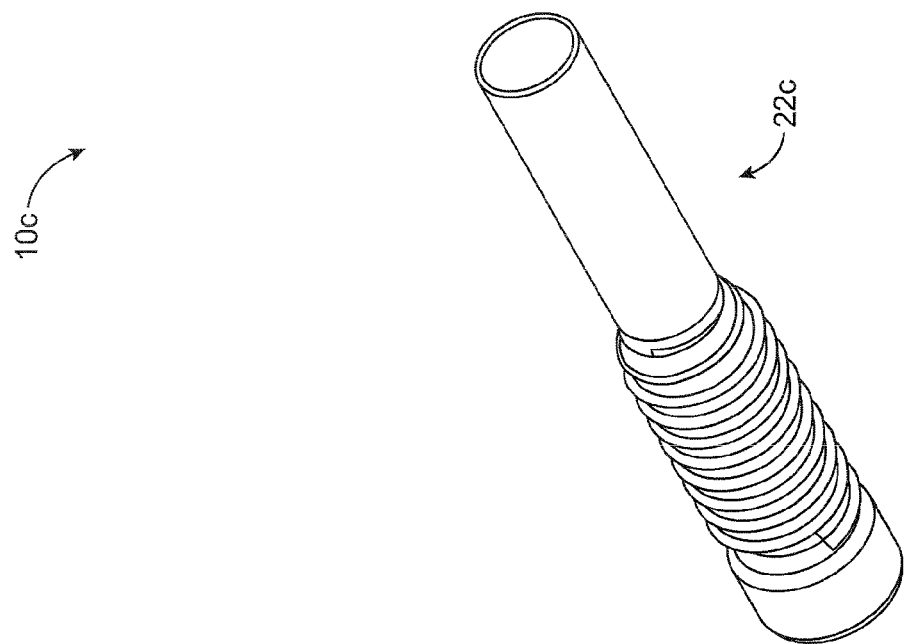

Alternatively, a stop 60c may comprise an annular shoulder formed on external unthreaded portion 28c of the inner screw member 20c as shown in a third preferred embodiment 10c illustrated in FIG. 5, where elements of similar structure as the first embodiment are designated by the same reference numerals followed by the lower case "c."

Figure 6:
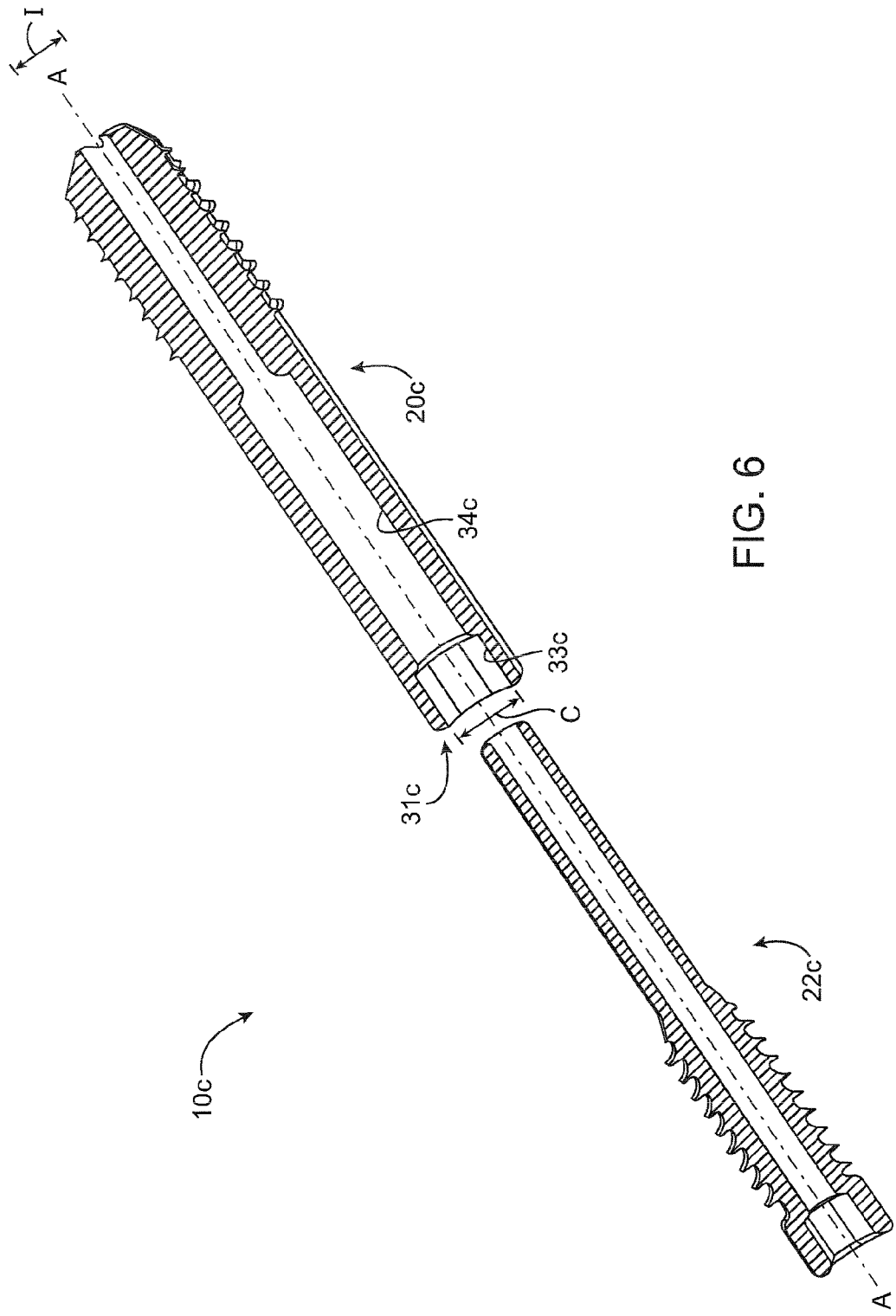
FIG. 6 is a cutaway exploded view of a third preferred embodiment of a collapsible bone screw apparatus.

FIG. 6 illustrates a third preferred embodiment 10c of the bone screw apparatus where elements of similar structure as the first embodiment are designated by the same reference numerals followed by the lower case "c". Whereas in the first preferred bone screw apparatus 10 in FIG. 1 the socket 33 is located at the medial end 36 of the hollow chamber 34 and is configured with a smaller cross-dimension C than the inner diameter I of the chamber 34, The socket 33c in the third preferred embodiment 10c in FIG. 6 may be located at the lateral end 31c of the hollow chamber 34c of the inner screw member 20c. In order to avoid blocking or interfering with the hollow chamber 34c receiving the outer screw member 22c, the socket 33c is configured with a cross-dimension, or width, "C" larger than the inner diameter "I" of the of the chamber 34c. Thus, a fastener may be used to engage the socket 33c at the lateral end 31c of the inner screw member 20c.

Figure 7:
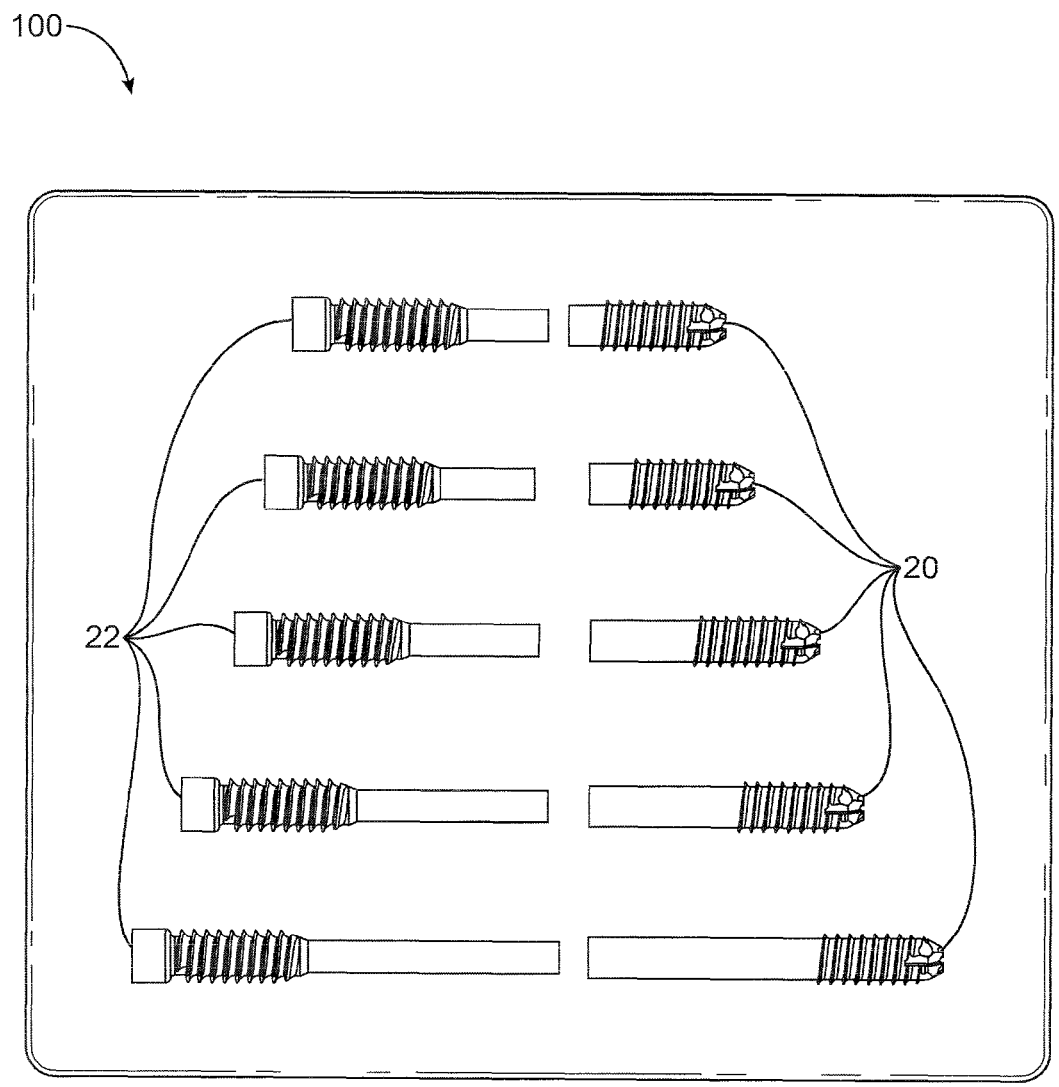
FIG. 7 is a diagram of a bone screw kit comprising a variety of inner screw members and a variety of outer screw members.

In FIG. 7, it will also be appreciated that a bone screw kit 100 of differently configured inner screw members 20 and outer screw members 22 are provided in order to provide a customized 2-piece bone screw apparatus. Accordingly, the preferred kit 100 provides flexibility in enabling a surgeon to select an inner screw member 20 of desired length and an outer screw member 22 of desired length to be coupled to the inner screw. The screw members 20, 22 may also vary in the pitch and length of the externally threaded portions. The flexibility of the kit 100 provides for a customized solution to a patient's particular fracture and bone, enabling a custom made 2-piece bone screw apparatus to be determined based upon the selection of the inner and outer screw members. The kit 100 may also comprise a variety of driving tools designed to mate with the screw members 20, 22.

In the preferred embodiment, each inner screw member 20 and outer screw member 22 has a preferred length of 40 to 85 mm, although the screw members may have shorter or longer lengths depending upon the need. The length of each screw member 20, 22 in the kit 100 preferably vary in increments of 5 mm. The overlap between a joined inner screw member 20 and outer screw member 22 may be a preferred minimum of 15 mm.

Figure 8:
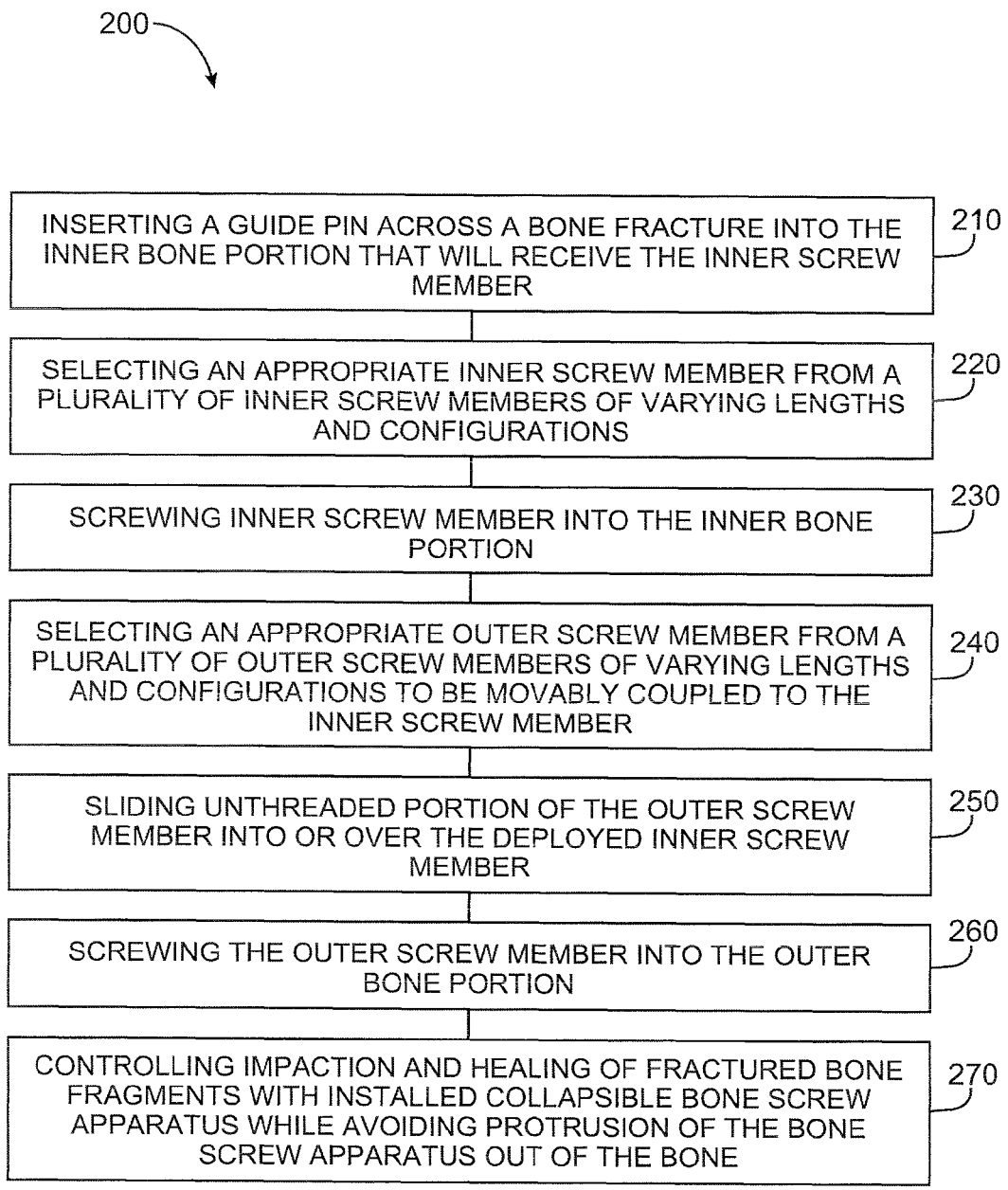
FIG. 8 is a diagram of a preferred method for surgically fastening fractured bone fragments.

In FIG. 8, a preferred method 200 of surgically fastening fractured bone fragments is illustrated. The method 200 comprises an optional step 210 of inserting a guide pin across a bone fracture into the inner bone portion that will receive the inner screw member. Step 220 comprises selecting an appropriate inner screw member from a plurality of inner screw members of varying lengths and configurations. For example, the inner screw members may vary in the pitch and length of the external threaded portions, in the sizes of the inner and outer diameters, in the configuration of the near openings for receiving a driving tool, and more.

In step 230, the inner screw member is screwed into the medial bone portion until it is properly seated near the inner wall of the cortical shell. Step 230 may be accomplished by configuring an opening of the inner screw—e.g., such as a hex shaped socket formed at a medial end of a hollow chamber of the inner screw—to receive a driving tool such as a hex key. The driving tool is used to rotate the inner screw until it is seated properly in the medial bone portion. It will be appreciated that step 230 is accomplished initially and independently from screwing the second, outer screw member.

Step 240 comprises selecting an appropriate outer screw member from a plurality of outer screw members of varying lengths and configurations to be movably coupled to the inner screw member. For example, the outer screw members may vary in the pitch and length of the external threaded portions, in the sizes of the inner and outer diameters, in the configuration of the near openings for receiving a driving tool, and more. In step 250, the unthreaded portion of the outer screw member is slid into or over the deployed inner screw member.

Step 260 comprises screwing the outer screw member into the outer bone portion such that it sufficiently gains purchase and is seated properly. Step 260 may be accomplished by configuring a lateral end of the outer screw—e.g., such as a hex shaped opening on a lateral end of the inner screw—to receive a driving tool such as a hex key. The driving tool is used to rotate the outer screw until it gains purchase with the lateral bone portion. At this point the outer screw member is connected to, and axially movable with, the inner screw member. Step 260 is preferably performed after step 230 of screwing the inner screw member into the medial bone portion. However, step 260 may also be performed concurrently with step 230 if a proper driver is used and the configurations of the sockets of the inner and outer screw members were substantially similar to mate with the driver. Also, the pitch of threads on both the inner screw member and the outer screw member would preferably be substantially similar to enable both screw members to be screwed into respective bone portions at the same time.

For convenience and simplicity, the sockets or openings of the inner screw members and outer screw members of a particular bone screw kit may be configured to receive the same driving tool, such that a single driving tool can be used to rotate all the inner and outer screw members of the kit. In the preferred method 200, the outer screw member is deployed separately from and subsequently to the deployment of the inner screw member. Thus, it will be appreciated that each screw member of the final two-piece bone screw apparatus is preferably installed independently.

Step 270 comprises controlling impaction and healing of fractured bone fragments with the installed collapsible bone screw apparatus while avoiding protrusion of the bone screw apparatus out of the bone. Step 270 includes allowing the inner screw member and outer screw member to collapse or telescope into one another as a result of bone impaction so as to shorten the overall length of the installed bone screw apparatus. Thus, step 270 comprises self-adjusting the overall length of the entire bone screw apparatus by virtue of the two screw members being axially movable with respect to each other.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A collapsible bone screw apparatus, comprising;
    an inner screw member having a first plurality of external threads configured to be directly attached to a first portion of bone tissue and located adjacent to a medial end, a non-threaded portion adjacent to a lateral end, an inner screw opening configured to enable the inner screw member to be screwed independently, and a hollow chamber having a non-threaded inner surface; and
    an outer screw member axially movable with respect to the inner screw member when deployed in order to provide an adjustable total length of the apparatus, the outer screw member having a second plurality of external threads configured to be directly attached to a second portion of bone tissue when the outer screw member is deployed, the outer screw member being rotationally free with respect to the inner screw member when the outer screw member is assembled to the inner screw member, wherein the outer screw member is configured to be screwed independently from the inner screw member in order to be secured to the second portion of bone tissue and to be assembled to the inner screw member without a connector.

2. The apparatus of claim 1, wherein the outer screw member comprises a lateral outer screw opening configured to enable the outer screw member to be screwed.

3. The apparatus of claim 1, wherein:
the inner screw member is substantially hollow; and
the outer screw member is configured to slide within the inner screw member.

4. The apparatus of claim 1, wherein:
the outer screw member is substantially hollow; and
the inner screw member is configured to slide within the outer screw member.

5. The apparatus of claim 1, further comprising a stop to provide a minimum for the total length.

6. The apparatus of claim 1, wherein rotational movement of the outer screw member with respect to the inner screw member does not necessarily adjust the total length of the apparatus.

7. The apparatus of claim 1, wherein:
the first plurality of external threads define a first outer diameter; and
the second plurality of external threads define a second outer diameter larger than the first outer diameter.

8. A collapsible bone screw apparatus, comprising;
an inner screw member having a first plurality of external threads configured to be directly attached to a first portion of bone tissue and located adjacent to a medial end, a non-threaded external portion adjacent to a lateral end, an inner screw opening configured to enable the inner screw member to be screwed, and a hollow chamber having a non-threaded inner surface; and
an outer screw member detachable from the inner screw member and axially movable with respect to the inner screw member in order to provide an adjustable total length of the apparatus, the outer screw member having a second plurality of external threads configured to be directly attached to a second portion of bone tissue when the outer screw member is assembled to the inner screw member, the outer screw member comprising a lateral outer screw opening configured to enable the outer screw member to be screwed,
wherein the outer screw member is both axially and rotationally movable with respect to the inner screw member when the outer screw member is assembled to the inner screw member, and
wherein the outer screw member is assembled to the inner screw member without a connector attaching the inner and outer screw members.

9. The apparatus of claim 8, wherein the inner screw member opening and the outer screw opening are configured to mate with a driving tool.

10. The apparatus of claim 8, wherein:
the inner screw member opening is configured to mate with a first driving tool; and
the outer screw opening is configured to mate with a second driving tool.

11. The apparatus of claim 8, wherein:
the outer screw member is configured to slide within the hollow chamber.

12. The apparatus of claim 8, wherein:
the outer screw member is substantially hollow; and
the inner screw member is configured to slide within the outer screw member.

13. The apparatus of claim 8, further comprising a stop to provide a minimum for the total length.

14. The apparatus of claim 8, wherein:
the inner screw opening comprises a first polygonal shaped opening; and
the outer screw opening comprises a second polygonal shaped opening.

15. The apparatus of claim 8, wherein:
the inner screw member comprises a hollow chamber having a lateral end and a medial end; and
the inner screw opening is located adjacent to the medial end of the hollow chamber.

16. The apparatus of claim 15, wherein the inner screw opening has a cross-dimension less than an inner diameter of the hollow chamber.

17. The apparatus of claim 8, wherein:
the inner screw member comprises a hollow chamber having a lateral end and a medial end; and
the inner screw opening is located adjacent to the lateral end of the hollow chamber.

18. The apparatus of claim 17, wherein the inner screw opening has a cross-dimension greater than an inner diameter of the hollow chamber.

19. The apparatus of claim 8, wherein rotational movement of the outer screw member with respect to the inner screw member does not necessarily adjust the total length of the apparatus.

20. The apparatus of claim 8, wherein:
the first plurality of external threads define a first outer diameter; and
the second plurality of external threads define a second outer diameter larger than the first outer diameter.

21. A collapsible bone screw apparatus, comprising;
an inner screw member having a first plurality of external threads configured to be directly attached to a first portion of bone tissue and located adjacent to a medial end, a non-threaded external portion adjacent to a lateral end, an inner screw opening configured to enable the inner screw member to be independently screwed into the first portion of bone tissue, and a hollow chamber having a non-threaded inner surface; and
an outer screw member detachable from the inner screw member and configured to be slidingly assembled to the inner screw member in a telescoping relationship without a connector, the outer screw member being axially movable with respect to the inner screw member when deployed in order to provide an adjustable total length of the apparatus, the outer screw member having a second plurality of external threads configured to be directly attached to a second portion of bone tissue when deployed, the outer screw member having a lateral outer screw opening configured to enable the outer screw member to be screwed into the second portion of bone tissue after the inner screw member is screwed into the first portion of bone tissue,
wherein the outer screw member is rotationally free with respect to the inner screw member when the outer screw member is assembled to the inner screw member.

22. The apparatus of claim 21, wherein the inner screw member opening and the outer screw opening are configured to mate with a driving tool.

23. The apparatus of claim 21, wherein:
the inner screw member opening is configured to mate with a first driving tool; and
the outer screw opening is configured to mate with a second driving tool.

24. The apparatus of claim 21, wherein:
the inner screw member is substantially hollow; and
the outer screw member is configured to slide within the inner screw member.

25. The apparatus of claim 21, wherein:
the outer screw member is substantially hollow; and
the inner screw member is configured to slide within the outer screw member.

26. The apparatus of claim 21, further comprising a stop to provide a minimum for the total length.

27. The apparatus of claim 21, wherein:
the inner screw opening comprises a first polygonal shaped opening; and
the outer screw opening comprises a second polygonal shaped opening.

28. The apparatus of claim 21, wherein:
the inner screw member comprises a hollow chamber having a lateral end and a medial end; and
the inner screw opening is located adjacent to the medial end of the hollow chamber.

29. The apparatus of claim 28, wherein the inner screw opening has a cross-dimension less than an inner diameter of the hollow chamber.

30. The apparatus of claim 21, wherein:
the inner screw member comprises a hollow chamber having a lateral end and a medial end; and
the inner screw opening is located adjacent to the lateral end of the hollow chamber.

31. The apparatus of claim 30, wherein the inner screw opening has a cross-dimension greater than an inner diameter of the hollow chamber.

32. The apparatus of claim 21, wherein rotational movement of the outer screw member with respect to the inner screw member does not necessarily shorten the total length of the apparatus.

33. The apparatus of claim 21, wherein:
the first plurality of external threads define a first outer diameter; and
the second plurality of external threads define a second outer diameter larger than the first outer diameter.

* * * * *